US008691872B2

(12) United States Patent
Lorimer et al.

(10) Patent No.: US 8,691,872 B2
(45) Date of Patent: Apr. 8, 2014

(54) DISPERSIONS OF RASAGILINE CITRATE (75) Inventors: Keith Lorimer, Lisburn (IE); David Engers, West Lafayette, IN (US)

(73) Assignee: Teva Pharmaceutical Industries Ltd., Petach-Tikva (IL)

( * ) Notice: Subject to any disclaimer, the term of this patent is extended or adjusted under 35 U.S.C. 154(b) by 167 days.

(21) Appl. No.: 13/192,082

(22) Filed: Jul. 27, 2011

(65) Prior Publication Data

US 2012/0059058 A1    Mar. 8, 2012

Related U.S. Application Data (60) Provisional application No. 61/400,369, filed on Jul. 27, 2010.

(51) Int. Cl.
*A01N 37/30* (2006.01)

(52) U.S. Cl.
USPC ........................................................ 514/554

(58) Field of Classification Search
USPC .................................................. 514/554, 657
See application file for complete search history.

(56) References Cited

U.S. PATENT DOCUMENTS

| | | | |
|---|---|---|---|
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A | 4/1999 | Youdim et al. | |
| 6,126,968 A | 10/2000 | Peskin et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,956,060 B2 | 10/2005 | Youdim et al. | |
| 7,396,860 B2 | 7/2008 | Blaugrund et al. | |
| 7,491,847 B2 | 2/2009 | Frenkel et al. | |
| 7,547,806 B2 | 6/2009 | Frenkel et al. | |
| 7,572,834 B1 | 8/2009 | Sterling et al. | |
| 7,598,420 B1 | 10/2009 | Sterling et al. | |
| 7,619,117 B1 | 11/2009 | Lidor-Hadas et al. | |
| 7,750,051 B2 | 7/2010 | Frenkel et al. | |
| 7,815,942 B2 | 10/2010 | Peskin | |
| 7,855,233 B2 | 12/2010 | Frenkel et al. | |
| 7,968,749 B2 | 6/2011 | Frenkel et al. | |
| 8,080,584 B2 | 12/2011 | Safadi et al. | |
| 8,143,315 B2 | 3/2012 | Stahl | |
| 8,334,409 B2 | 12/2012 | Frenkel | |
| 2004/0127577 A1 | 7/2004 | Blaugrund et al. | |
| 2006/0018957 A1 | 1/2006 | Lerner et al. | |
| 2006/0094783 A1 | 5/2006 | Youdim | |
| 2007/0100001 A1 | 5/2007 | Youdim | |
| 2007/0232700 A1 | 10/2007 | Blaugrund et al. | |
| 2009/0062400 A1 | 3/2009 | Oron et al. | |
| 2009/0076160 A1 | 3/2009 | Lendvai et al. | |
| 2009/0111892 A1 | 4/2009 | Patashnik et al. | |
| 2009/0136549 A1 | 5/2009 | Lin et al. | |
| 2009/0181086 A1 | 7/2009 | Safadi et al. | |
| 2009/0312436 A1 | 12/2009 | Levy et al. | |
| 2010/0008983 A1 | 1/2010 | Safadi et al. | |
| 2010/0010095 A1 | 1/2010 | Frenkel | |
| 2010/0137447 A1 | 6/2010 | Lehmann et al. | |
| 2010/0144887 A1 | 6/2010 | Frenkel et al. | |
| 2010/0145101 A1 | 6/2010 | Frenkel et al. | |
| 2010/0168239 A1 | 7/2010 | Poewe | |
| 2010/0189788 A1 | 7/2010 | Safadi et al. | |
| 2010/0189790 A1 | 7/2010 | Safadi et al. | |
| 2010/0189791 A1 | 7/2010 | Safadi et al. | |
| 2010/0234636 A1 | 9/2010 | Stahl | |
| 2011/0130466 A1 | 6/2011 | Lorenzl | |
| 2011/0152381 A1 | 6/2011 | Frenkel et al. | |
| 2011/0313050 A1 | 12/2011 | Rimkus et al. | |
| 2012/0003310 A1 | 1/2012 | Safadi et al. | |
| 2012/0029087 A1 | 2/2012 | Petit et al. | |
| 2012/0059058 A1 | 3/2012 | Lorimer et al. | |
| 2012/0101168 A1 | 4/2012 | Bahar et al. | |
| 2012/0238636 A1 | 9/2012 | Patashnik et al. | |
| 2012/0263789 A1 | 10/2012 | Safadi et al. | |
| 2013/0089610 A1 | 4/2013 | Safadi et al. | |
| 2013/0089611 A1 | 4/2013 | Ulanenko et al. | |
| 2013/0089612 A1 | 4/2013 | Safadi et al. | |

FOREIGN PATENT DOCUMENTS

| | | |
|---|---|---|
| WO | WO 2010/070090 | 6/2010 |
| WO | WO 2011/003938 | 1/2011 |

OTHER PUBLICATIONS

PCT International Preliminary Report on Patentability, issued Jan. 29, 2013 in connection with PCT/US2011/045569, filed Jul. 27, 2011.
U.S. Appl. No. 12/283,107, filed Sep. 8, 2008 (Sterling et al.) (pending claims and specification).
U.S. Appl. No. 13/647,658, filed Oct. 9, 2012 (Ulanenko et al.) (pending claims and specification).
U.S. Appl. No. 13/647,665, filed Oct. 9, 2012 (Safadi et al.) (pending claims and specification).
U.S. Appl. No. 13/647,622, filed Oct. 9, 2012 (Safadi et al.) (pending claims and specification).
U.S. Appl. No. 13/651,307, filed Oct. 12, 2012 (Levy et al.) (pending claims and specification).
International Search Report and Written Opinion of the International Searching Authority for International Application No. PCT/US2011/045569, issued Dec. 14, 2011.
U.S. Appl. No. 13/859,625, filed Apr. 9, 2013, Levy, et al.
U.S. Appl. No. 14/016,960, filed Sep. 3, 2013, Lehmann et al.
U.S. Appl. No. 13/967,240, filed Aug. 14, 2013, Rimkus et al.
May 17, 2013 Office Action issued by the Russian Patent Office in connection with Russian Patent Application No. 2013108256.
Amendment filed in response to May 17, 2013 Office Action issued by the Russian Patent Office in connection with Russian Patent Application No. 2013108256.
Jadhav et al. (2009) "Glass transition temperature: Basics and application in pharmaceutical sector," Asian Journal of Pharmaceutics, 3(2):82-89.

*Primary Examiner* — Jason M Sims
*Assistant Examiner* — Ibrahim D Bori
(74) *Attorney, Agent, or Firm* — John P. White; Gary J. Gershik; Cooper & Dunham LLP (57) ABSTRACT

The subject invention provides a solid dispersion of rasagiline citrate, a composition and a process for the manufacture thereof.

9 Claims, 3 Drawing Sheets

DISPERSIONS OF RASAGILINE CITRATE

This application claims benefit of U.S. Provisional Application No. 61/400,369, filed Jul. 27, 2010, the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514 disclose R(+)-N-propargyl-1-aminoindan ("R-PAI"), also known as rasagiline. U.S. Pat. No. 6,126,968 and PCT International Application Publication No. WO 95/11016 disclose pharmaceutical compositions comprising rasagiline. Rasagiline has been reported to be a selective inhibitor of the B-form of the enzyme monoamine oxidase ("MAO-B") and is useful in treating Parkinson's disease and various other conditions by inhibition of MAO-B in the brain.

A formulation of rasagiline mesylate is approved for treating Parkinson's disease either as monotherapy or as an adjunct with other treatments. See, e.g. AZILECT®, Physicians' Desk Reference 2009 (PRD, 63rd Edition).

AZILECT® is indicated for the treatment of the signs and symptoms of idiopathic Parkinson's disease as initial monotherapy and as adjunct therapy to levodopa. Rasagiline, the active ingredient of AZILECT®, is rapidly absorbed, reaching peak plasma concentration ($C_{max}$) in approximately 1 hour. The absolute bioavailability of rasagiline is about 36%. (AZILECT® Product Label, May 2006).

While not previously identified as a problem for rasagiline, there remains a need for a solid dispersion of rasagiline with polymeric pharmaceutical excipients that exhibits suitable handling properties.

SUMMARY OF THE INVENTION

The subject invention provides a solid dispersion of at least one polymeric pharmaceutical excipient and rasagiline or a pharmaceutically acceptable salt thereof.

The subject invention also provides a pharmaceutical composition comprising the solid dispersion described herein.

The subject invention further provides a process for making the solid dispersion described herein, comprising:
  a) dissolving a mixture of rasagiline or the pharmaceutically acceptable salt thereof, and the at least one polymeric pharmaceutical excipient in a solvent to form a solution; and
  b) removing the solvent from the solution.

The subject invention yet further provides a process for making the solid dispersion described herein, comprising:
  a) obtaining a solid mixture of rasagiline or the pharmaceutically acceptable salt thereof, and the at least one polymeric pharmaceutical excipient; and
  b) grinding the mixture.

DETAILED DESCRIPTION OF THE INVENTION

The subject invention provides a solid dispersion of at least one polymeric pharmaceutical excipient and rasagiline or a pharmaceutically acceptable salt thereof.

In an embodiment of the solid dispersion, the at least one polymeric pharmaceutical excipient is a water soluble polymeric pharmaceutical excipient.

In another embodiment of the solid dispersion the pharmaceutically acceptable salt of rasagiline is rasagiline citrate.

In yet another embodiment of the solid dispersion, the rasagiline citrate is mono-rasagiline citrate.

In yet another embodiment of the solid dispersion, the at least one polymeric pharmaceutical excipient is polyvinylpyrrolidone, hydroxypropyl methylcellulose, hydroxypropyl methylcellulose acetate succinate, or hydroxypropyl methylcellulose phthalate.

In yet another embodiment of the solid dispersion, the at least one polymeric pharmaceutical excipient is a co-polymer.

In yet another embodiment of the solid dispersion, the co-polymer is polyvinylpyrrolidone-vinyl acetate or methacrylic acid-ethyl acrylate.

In yet another embodiment of the solid dispersion, the co-polymer is methacrylic acid-ethyl acrylate.

In yet another embodiment of the solid dispersion, $T_g$ of the solid dispersion is at least 20° C. higher than that of rasagiline or a pharmaceutically acceptable salt thereof.

The subject invention also provides a pharmaceutical composition comprising the solid dispersion described herein.

The subject invention further provides a process for making the solid dispersion of rasagiline citrate described herein, comprising:
  a) combining a mixture of rasagiline free base and the at least one polymeric pharmaceutical excipient in a solvent to form a solution;
  b) adding citric acid to the solution; and
  c) removing the solvent from the solution.

The subject invention further provides a process for making the solid dispersion of rasagiline citrate described herein, comprising:
  a) dissolving a mixture of rasagiline or the pharmaceutically acceptable salt thereof, and the at least one polymeric pharmaceutical excipient in a solvent to form a solution; and
  b) removing the solvent from the solution.

In an embodiment of the process, the pharmaceutically acceptable salt of rasagiline is rasagiline citrate.

In another embodiment of the process, the rasagiline citrate is mono-rasagiline citrate.

In an embodiment of the process, the solvent is methanol, ethanol, acetone, dichloromethane, dioxane and water, or a mixture of at least two thereof.

In another embodiment of the process, step b) is performed at a temperature of between about 55° C. and 80° C. by rotary evaporation.

In yet another embodiment of the process, in step b) the solvent is removed by lyophilization.

The subject invention yet further provides a process for making the solid dispersion of rasagiline citrate described herein, comprising:

a) combining a mixture of rasagiline free base, the at least one polymeric pharmaceutical excipient, and citric acid; and b) grinding the mixture.

The subject invention yet further provides a process for making the solid dispersion of rasagiline citrate described herein, comprising:

a) obtaining a solid mixture of rasagiline or the pharmaceutically acceptable salt thereof, and the at least one polymeric pharmaceutical excipient; and b) grinding the mixture.

In an embodiment of the process, the pharmaceutically acceptable salt of rasagiline is rasagiline citrate.

In another embodiment of the process, the rasagiline citrate is mono-rasagiline citrate.

In yet another embodiment of the process, step b) is performed by dry milling the mixture.

In yet another embodiment of the process, step b) is performed by wet milling the mixture with a solvent.

In yet another embodiment of the process, the solvent is methanol or acetone.

In yet another embodiment of the process, step b) is performed at a temperature below 0° C.

In yet another embodiment of the process, step b) is performed at a temperature below −10° C.

In yet another embodiment of the process, step b) is performed at a temperature below −25° C.

In yet another embodiment of the process, step b) is performed at a temperature below −50° C.

In yet another embodiment of the process, step b) is performed at a temperature below −100° C.

In yet another embodiment of the process, step b) is performed at a temperature below −150° C.

The subject invention yet further provides a method of treating a human subject afflicted with Parkinson's disease comprising administering to the human subject an amount of the pharmaceutical composition of claim 8, effective to treat the human subject.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

Citric acid is a weak organic acid, and is triprotic. Therefore, the rasagiline citrate described herein may exist in mono-, di- or tri-rasagiline citrate form or a mixture thereof.

As used herein, an example of an immediate release formulation of rasagiline is an AZILECT® Tablet containing rasagiline mesylate.

As used herein, a polymer is a large molecule composed of repeating structural units typically connected by covalent chemical bonds.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

As used herein, a "pharmaceutically acceptable salt" of rasagiline includes citrate, tannate, malate, mesylate, maleate, fumarate, tartrate, esylate, p-toluenesulfonate, benzoate, acetate, phosphate and sulfate salts. For the preparation of pharmaceutically acceptable acid addition salts of the compounds of the invention, the free base can be reacted with the desired acids in the presence of a suitable solvent by conventional methods.

Rasagiline can also be used in its free base form. A process of manufacture of the rasagiline free base is described in PCT publication WO 2008/076348, the contents of which are hereby incorporated by reference.

As used herein, an "isolated" compound is a compound that has been separated from the crude reaction mixture in which it formed by an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to separate the chemical entity and the composition.

As used herein, a "glass transition temperature ($T_g$)" of a solid is the temperature where the solid goes from a rigid state to a flexible state. At $T_g$, a polymer undergoes a phase transition from a hard, glass-like state to a flexible, rubber-like state. The $T_g$ temperature values listed herein were determined based upon half-height of the step change or "S" shape curve seen in DSC data.

As used herein, a polymer is a large molecule composed of repeating structural units typically connected by covalent chemical bonds.

As used herein, a "solid dispersion" is a drug-containing pharmaceutical bulk substance in which the drug is dispersed in a pharmaceutical excipient such as a polymer, a co-polymer, or a mixture thereof.

Specific examples of pharmaceutically acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The pharmaceutical dosage forms may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or nonaqueous solution or emulsion; for rectal administration the invention provides suppositories with hydrophilic or hydrophobic vehicles; for topical application as ointments; and for transdermal delivery the invention provides suitable delivery systems as known in the art.

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

One type of oral dosage forms of the present invention relates to delayed release formulations. Such formulations may be comprised of an acid resistant excipient which prevents the dosage form or parts thereof from contacting the acidic environment of the stomach. The acid resistant excipient may coat the rasagiline in the form of an enteric coated tablet, capsule, or gelatin capsule. Enteric coating, in the context of this invention, is a coating which prevents the dissolution of an active ingredient in the stomach. Specific examples of pharmaceutically acceptable carriers and excipients that may be used to formulate such delayed release formulations are described, e.g., in International Application Publication No. WO 06/014973, hereby incorporated by reference in its entirety.

Another type of oral dosage forms of the present invention relates to fast disintegrating formulations which provide a means to avoid the absorption of rasagiline in the stomach, and to eliminate the need for swallowing tablets, by absorption of rasagiline into the body before reaching the stomach. Such absorption of rasagiline can be accomplished by contact with the buccal, sublingual, pharyngeal and/or esophageal mucous membranes. To accomplish this, the fast disintegrating formulations were designed to rapidly disperse within the mouth to allow maximum contact of rasagiline with the buccal, sublingual, pharyngeal and/or esophageal mucous membranes. Specific examples of pharmaceutically acceptable carriers and excipients that may be used to formulate such fast disintegrating formulations are described, e.g., in International Application Publication No. WO 03/051338, hereby incorporated by reference in its entirety.

Other pharmaceutical compositions of the present invention include transdermal patches. Transdermal patches are medicated adhesive patches placed on the skin to deliver a time-released dose of medication through the skin and into the bloodstream. A wide variety of pharmaceuticals can be delivered through transdermal patches. Some pharmaceuticals must be combined with other substances, for example alcohol, to increase their ability to penetrate the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. (Wikipedia; and Remington, The Science and Practice of Pharmacy, 20$^{th}$ Edition, 2000)

In reservoir type patches, a drug is combined with a nonvolatile, inert liquid, such as mineral oil, whereas in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST, PRESENT, FUTURE," Molecular Interventions, 4:308-312)

The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Delivery)

In all of its aspects, the present invention provides pharmaceutical dosage forms useful for treating a condition selected from the group consisting of: Parkinson's disease (PD), brain ischemia, stroke, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, Multiple Sclerosis (MS), schizophrenia, affective illness, Amyotrophic Lateral Sclerosis, Restless Legs Syndrome (RLS), hearing loss, Multiple System Atrophy (MSA), Glucoma, modifying Parkinson's disease, and Progressive Supranuclear Palsy (PSP), but with a reduced risk of peripheral MAO inhibition that is typically associated with administration of rasagiline with known oral dosage forms.

A conventional method for the manufacture of a solid dispersion relates to a fusion process which is characterized by melting a drug substance and a polymeric pharmaceutical excipient together at elevated temperature and, then, cooling the melt to solidify. Another conventional method for the manufacture of a solid dispersion relates to a solvent process which is characterized by dissolving a drug substance and a polymeric pharmaceutical excipient in an appropriate solvent and, then, removing the solvent. Additional method for the manufacture of a solid dispersion relates to mixing a drug substance and a polymeric pharmaceutical excipient through milling.

Generally, a phase-separated dispersion will exhibit two $T_g$ values, whereas a molecular dispersion will exhibit a single $T_g$.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

This invention will be better understood from the experimental details which follow. However, one skilled in the art will readily appreciate that the specific methods and results discussed are merely illustrative of the invention as described more fully in the claims which follow thereafter.

Experimental Details

A solid dispersion screen was carried out using rasagiline citrate and pharmaceutical excipients of polymers. Dispersions were prepared using several techniques including rotary evaporation from solution, cryogrinding dry components and lyophilization. Samples were analyzed by modulated Differential Scanning calorimetry (DSC) to determine glass transition temperatures ($T_g$). A slight excess of citric acid was used in most dispersions i.e. 0.7:1 mol of rasagiline: citric acid.

The pharmaceutical excipients of polymers used in the following example are listed in the table below:

| Excipient | Abbreviation |
|---|---|
| polyvinylpyrrolidone-vinyl acetate | PVP-VA |
| polyvinylpyrrolidone | PVP K-29/32 |
| polyvinylpyrrolidone | PVP K-90 |
| hydroxypropyl methylcellulose | HPMC |
| hydroxypropyl methylcellulose - acetate succinate | HPMC-AS |
| hydroxypropyl methylcellulose - phthalate | HPMC-P |
| methacrylic acid ethyl acrylate copolymer | Eudragit L-100 |

These pharmaceutical excipients of polymers each exhibits characteristics as listed in the following table.

| Excipient | Observation[a] |
|---|---|
| Eudragit L-100 | small white particles, no B/E |
| HPMC | small rod-like fragments, B/E |
| HPMC-AS | small particles, some B/E |
| HPMC-P | small, irregular fragments, B/E |
| PVP K-29/32 | small particles, B/E |
| PVP K-90 | small particles, B/E |

[a]Observations by light microscopy. B = birefringence, E = extinction.

EXAMPLE 1

Preparation of Mono-Rasagiline Citrate Salt

In the following experiment, rasagiline base was mixed with citric acid (1:1 mol:mol) and then methanol was added to the mixture. After stirring and complete dissolution of solids, the solution was evaporated under vacuum in rotary evaporator at bath temperature 60° C. The resulting foamy substance was dried under vacuum to obtain mono-rasagiline citrate.

TABLE 1

Preparation of Mono-Rasagiline Citrate Salt

| Sample No | Solvent/Conditions[a] | Observations | Analysis[b] | Result |
|---|---|---|---|---|
| 1 | MeOH/RE @60° C., vacuum dried | foamy substance | HSM | At 40° C., solids become gel-like, all become gel at 80° C. |
| | | | cyclic DSC | $T_g = 18°$ C. |
| | | | Modulated DSC | $T_g = 16°$ C. |

[a]RE = rotary evaporation,
[b]HSM = hotstage microscopy, DSC = differential scanning calorimetry.

EXAMPLE 2

Solid Dispersion of Rasagiline Citrate Prepared by Rotary Evaporation

The experiments conducted in this example are listed below in Table 2. In each of the experiments, rasagiline free base, excipient, and citric acid were combined and mixed in the corresponding solvent. A solid dispersion was prepared from the mixture by rotary evaporation of the solvent at conditions listed in Table 2 below.

TABLE 2

| Excipient[a] | Exp. No.* | Solvent[b] | Conditions[d] | Observation[e] |
|---|---|---|---|---|
| Eudragit L-100 (1:1) | 1 | EtOH | RE @70° C. | glassy solids, some which show extinction |
| | | | vac. dried | glassy solids |
| Eudragit L-100 (70:30) | 2[c] | MeOH | RE @65° C., vac. dried | handleable white powder, glassy fragments, a few extinguish |
| Eudragit L-100 (75:25) | 3[c] | MeOH | RE @60° C., vac. dried | white solid, stored @ −13° C. |
| HPMC (1:1) | 4 | MeOH: H$_2$O | did not dissolve, sample discarded | — |
| HPMC (75:25) | 5 | MeOH: DCM | RE @60° C., vac. dried | gel formed, plastic-like film after vac dried w/B, stored @ −13° C. |

TABLE 2-continued

| Excipient[a] | Exp. No.* | Solvent[b] | Conditions[d] | Observation[e] |
|---|---|---|---|---|
| HPMC (70:30) | 6 | MeOH: H$_2$O | sample did not dissolve | — |
| HPMC-AS (1:1) | 7 | MeOH: ACN | RE @80° C. vac. dried | foamy substance, very sticky gel |
| HPMC-AS (70:30) | 8[c] | Acetone: MeOH | RE @55° C., vac. dried | many solids clung to side of vial, scraped down solids are handleable and off-white. Glassy fragments, no B/E |
| HPMC-AS (75:25) | 9[c] | MeOH: DCM | RE @60° C., vac. dried | white foam, dry white powder when dried |
| HPMC-P (1:1) | 10 | Acetone: H$_2$O | RE @50° C. | foam with solid particles dispersed, became gel |
| HPMC-P (75:25) | 11 | MeOH: DCM | RE @60° C., vac. dried | white foam, white powder when dried |
| HPMC-P (90:10) | 12[c] | Acetone: DCM | RE @55° C., vac. dried | tacky white solids, glassy fragments |
| PVP-VA (1:1) | 13 | EtOH | RE @70° C. | glassy solids, slightly sticky to spatula, no B/E under microscope |
|  | 14[c] | DCM | vac. dried | glassy solids |
|  |  |  | — | sample did not dissolve |
| PVP-VA (70:30) | 15[c] | Acetone: MeOH | RE @55° C., vac. dried | handleable white solids, glassy fragments, no B/E |
| PVP-VA (90:10) | 16[c] | Acetone: DCM | RE @55° C., vac. dried | fine white powder, easily handled, uniform glassy fragments |
| PVP K-29/32 (1:1) | 17 | Acetone: EtOH | RE @60° C. vac. dried | foamy substance, gel like glassy material, became powder when touched with spatula. Glassy solids under microscope, no B/E |
| PVP K-29/32 (75:25) | 18 | Acetone: MeOH | RE @60° C., vac dried | white sticky solid, no B/E, dry white solid when dried, stored @ −13° C. |
| PVP K-90 (1:1) | 19 | Acetone: EtOH | RE @70° C. | glassy solids, no B/E |
| PVP K-90 (70:30) | 20[c] | DCM: MeOH | RE @50° C., vac. dried | handleable white powder, glassy fragments, few extinguish |
| PVP K-90 (75:25) | 21[c] | MeOH: acetone | RE @60° C., vac. dried | white foam, no B/E, dy white solid when dried, stored @ −13° C. |
| PVP K-90 (90:10) | 22[c] | Acetone: DCM | RE @55° C., vac. dried | tacky white solids, glassy fragments |

*the molar ratio of rasagiline:citric acici is 1:1 unless indicated otherwise
[a]Excipient:Rasagiline ratio (weight/weight)
[b]Excipient and Rasagiline dissolved in solvent, followed by addition of citric acid in a 1:1 molar ratio.
[c]0.7:1 molar ratio of rasagiline:citric acid
[d]RE = rotary evaporation.
[e]observations by light microscopy. B = birefringence, E = extinction

EXAMPLE 3

Solid Dispersion of Rasagiline Citrate Prepared by Grinding

The experiments conducted in this example are listed below in Table 3. In each of the experiments, rasagiline free base, excipient, and citric acid were combined and mixed. A solid dispersion was prepared from the mixture by dry milling, wet milling, or cryo-grinding the mixture at conditions listed in Table 3 below.

TABLE 3

| Excipient[a] | Exp. No.* | Conditions | Observation[c] |
|---|---|---|---|
| HPMC (60:40) | 1[b] | dry milled, 30 Hz, 15 minutes | white powder, solids present with B/E, no single phase |
|  | 2 | wet milled w/ acetone, 30 Hz, 10 minutes | fine white powder and sticky solids, fragments with B/E present |
| HPMC (70:30) | 3 | cryogrind grind 2 minutes, 5 cycles, rate = 10 | small white particles, no B/E |
| HPMC-P (1:1) | 4 | cryogrind grind 2 minutes, 3 cycles, rate = 10 | small white particles, no B/E |
| HPMC-P (70:30) | 5 | cryogrind grind 2 minutes, 5 cycles, rate = 10 | small white particles, approx same size, shape, no B/E |
| PVP-VA (1:1) | 6[b] | dry milled, 30 Hz, 15 minutes | white powder, solids present with B/E, pockets of differing morphology |
|  | 7 | wet milled w/MeOH, 30 Hz, 10 minutes | fine white powder and sticky solids, pockets of birefringent material |
| PVP-VA (70:30) | 8 | cryogrind grind 2 minutes, 5 cycles, rate = 10 | white fine particles with no B/E |
| PVP K-29/32 (70:30) | 9 | cryogrind grind 2 minutes, 5 cycles, rate = 10 | small white particles approx same size, no B/E |

TABLE 3-continued

| Excipient[a] | Exp. No.* | Conditions | Observation[c] |
|---|---|---|---|
| PVP K-90 (60:40) | 10[b] | cryogrind grind 2 minutes, 5 cycles, rate = 10 | white fine powder. Appears as single phase with same size, morphology |

*the molar ratio of rasagiline:citric acid is 1:1 unless indicated otherwise
[a]Excipient:Rasagiline ratio (weight/weight)
[b]0.7:1 molar ratio of Rasagiline:citric acid
[c]observations by light microscopy. B = birefringence, E = extinction

EXAMPLE 4

Solid Dispersion of Rasagiline Citrate Prepared by Lyophilization

The experiments conducted in this example are listed below in Table 4. In each of the experiments, rasagiline free base, excipient, and citric acid were combined and mixed in the corresponding solvent. A solid dispersion was prepared from the mixture by lyophilization at conditions listed in Table 4 below.

TABLE 4

| Excipient[a] | Exp. No. | Solvent | Conditions | Observation |
|---|---|---|---|---|
| HPMC-P (7:3) | 1[b] | dioxane | lyophilize overnight | fluffy white powder |
| HPMC-AS (7:3) | 2[b] | dioxane | lyophilize overnight | fluffy white powder |
| HPMC-P (7:3) | 3[b] | dioxane-water (1:1) | lyophilize overnight | fluffy white powder |
| PVP-VA (7:3) | 4[b] | dioxane-water (1:1) | lyophilize overnight | fluffy white powder |

[a]Excipient:Rasagiline ratio (weight/weight)
[b]0.7:1 molar ratio of Rasagiline:citric acid

EXAMPLE 5

Analysis of Dispersions of Rasagiline Citrate

Samples of dispersion of rasagiline citrate obtained in Examples 2-4 were analyzed and the results are summarized in Table 5 below.

TABLE 5

| Excipient[a] | Sample No. | Prep Method[b] | Analysis | Result | $T_g$ calc[c] |
|---|---|---|---|---|---|
| Eudragit ® L 100 (1:1) | 1[d] | RE | MDSC | $T_g$ = 15° C. | 60° C. |
| Eudragit ® L 100 (30:70) | 2 | RE | MDSC | $T_g$ = 19° C. | 82° C. |
| HPMC (30:70) | 3 | cryomill | MDSC | $T_g$ = 32° C., 126° C. | 106° C. |
| HPMC-AS (30:70) | 4 | RE | MDSC | $T_g$ = 17° C., 100° C. | 90° C. |
| HPMC-AS (30:70) | 5 | lyophilization | MDSC | $T_g$ = 17° C. | 90° C. |
| HPMC-P (1:1) | 6[d] | cryomill | MDSC | $T_g$ = 25° C. | 69° C. |
| HPMC-P (25:75) | 7 | RE | MDSC | $T_g$ = 8° C. | 103° C. |
| HPMC-P (30:70) | 8 | lyophilization | MDSC | $T_g$ = 29° C. | 96° C. |
| HPMC-P (30:70) | 9 | cryomill | MDSC | $T_g$ = 27° C. | 96° C. |
| HPMC-P (10:90) | 10[d] | RE | MDSC | — | 127° C. |
| PVP K-29/32 (1:1) | 11[d] | RE | MDSC | $T_g$ = 3° C. | 75° C. |
| PVP K-29/32 (30:70) | 12 | cryomill | MDSC | $T_g$ = 29° C. | 106° C. |
| PVP K-29/32 (30:70) | 13 | lyophilization | MDSC | $T_g$ = 30° C. | 106° C. |
| PVP K-29/32 (25:75) | 14 | RE | MDSC | $T_g$ = 17° C. | 106° C. |
| PVP K-90 (1:1) | 15[d] | RE | MDSC | $T_g$ = 18° C. | 78° C. |
| PVP K-90 (30:70) | 16 | RE | MDSC | $T_g$ = 34° C. | 111° C. |
| PVP K-90 (40:60) | 17 | cryomill | MDSC | $T_g$ = 39° C. | 94° C. |
| PVP K-90 (10:90) | 18 | RE | MDSC | — | 151° C. |
| PVP-VA (1:1) | 19[d] | RE | MDSC | $T_g$ = 16° C., 77° C. | 56° C. |
| PVP-VA (30:70) | 20 | RE | MDSC | $T_g$ = 38° C. | 76° C. |
| PVP-VA (30:70) | 21 | lyophilization | MDSC | $T_g$ = 22° C. | 76° C. |

TABLE 5-continued

| Excipient[a] | Sample No. | Prep Method[b] | Analysis | Result | $T_g$ calc[c] |
|---|---|---|---|---|---|
| PVP-VA (30:70) | 22 | cryomill | MDSC | $T_g = 26°$ C. | 76° C. |

[a]Rasagiline:excipient weight ratio listed in parentheses.
[b]RE = rotary evaporation.
[c]$T_g$ value for ideal dispersion calculated using Fox equation.
[d]1:1 molar ratio of Rasagiline:citric acid. All other samples contain slight excess of citric acid

EXAMPLE 6

Stressing of Dispersions of Rasagiline Citrate

Stability of the dispersions of rasagiline citrate obtained in Examples 2-4 was studied at the conditions listed in Table 6 below. The results are also summarized in Table 6 below.

TABLE 6

| Excipient[a] | Sample No. | Conditions[b] | Duration | Observation[c] |
|---|---|---|---|---|
| Eudragit L-100 (70:30) | 1 | 75% RH | 2 hours | no change |
| | | | 4 hours | no change |
| | | | 6 hours | no change |
| | | | 8 hours | no change |
| | | | 24 hours | pooling of solids, needles present |
| | | | 5 days | slight pooling of solids w/moisture |
| HPMC-AS (70:30) | 2 | 75% RH | 2 hours | no change |
| | | | 4 hours | no change |
| | | | 6 hours | no change |
| | | | 8 hours | no change |
| | | | 24 hours | pooling of solids w/ moisture |
| | | | 5 days | pooling of solids w/ moisture |
| HPMC-P (70:30) | 3 | 75% RH | 2 hours | no change |
| | | | 4 hours | no change |
| | | | 6 hours | no cnange |
| | | | 8 hours | pooling or solids |
| | | | 24 hours | pooling of solids w/ moisture |
| | | | 5 days | deliquesced |
| PVP K-29/32 (70:30) | 4 | 75% RH | 2 hours | no change |
| | | | 4 hours | pooling of solids |
| | | | 6 hours | pooling of solids |
| | | | 8 hours | pooling of solids |
| | | | 24 hours | deliquesced |
| PVP K-90 (70:30) | 5 | 75% RH | 2 hours | no change |
| | | | 4 hours | no change |
| | | | 6 hours | no change |
| | | | 8 hours | no change |
| | | | 24 hours | deliquesced |
| PVP-VA (70:30) | 6 | 75% RH | 2 hours | no change |
| | | | 4 hours | no change |
| | | | 6 hours | pooling of solids |
| | | | 8 hours | pooling of solids |
| | | | 24 hours | deliquesced |
| Rasagiline Citrate | 7 | 75% RH | 2 hours | pooling of solids |
| | | | 4 hours | deliquesced |
| | | | 6 hours | deliquesced |
| | | | 8 hours | deliquesced |
| | | | 24 hours | deliquesced |
| HPMC-P (1:1) | 8 | 75% RH | 1 day | solids pooling together with moisture |
| PVP-VA (70:30) | 9 | 75% RH | 1 day | solids deliquesced |
| PVP K-90 (70:30) | 10 | 75% RH | 1 day | slight pooling of moisture around solids |

[a]polymer:drug weight ratio listed in parentheses.
[b]RH = relative humidity.
[c]Observations made visually using light microscopy.

EXAMPLE 7

Additional Preparation of Solid Dispersion of Rasagiline Citrate

In Examples 2-4, rasagiline citrate was formed in-situ by combining rasagiline free base, excipient, and citric acid in the preparation of solid dispersion of rasagiline citrate. Alternatively, the solid dispersion of rasagiline citrate can be prepared by obtaining rasagiline citrate salt first. The rasagiline citrate can be obtained by reacting rasagiline free base with citric acid in the presence of a suitable solvent by conventional methods, e.g. the process described in Example 1.

The rasagiline citrate obtained can then be mixed with the excipient listed in Table 2 to prepare the solid dispersion of rasagiline citrate by the rotary evaporation as described in Example 2. The rasagiline citrate obtained can also be mixed with the excipient listed in Table 3 to prepare the solid dispersion of rasagiline citrate by dry milling, wet milling, or cryo-grinding as described in Example 3. The rasagiline citrate obtained can further be mixed with the excipient listed in Table 4 to prepare the solid dispersion of rasagiline citrate by lyophilization as described in Example 4.

Discussion of Examples 1-6

The plasticizing effect of water as well as the low $T_g$ of rasagiline citrate has generally resulted in dispersions with low $T_g$ values. $T_g$ of mono-rasagiline citrate was ~17° C. by DSC.

Most of the solid dispersions of rasagiline citrate prepared appeared to be phase-separated by MDSC. In addition, $T_g$ of some of the solid dispersions of rasagiline citrate prepared was not observed due to decomposition of rasagiline at elevated temperatures.

Dispersions containing PVP K90 and PVP-VA have shown the largest increase in $T_g$ with high polymer loadings but both deliquesced when stressed under high relative humidity for 1 day.

All solid dispersions of rasagiline citrate prepared using methods described in Examples 2-4 have resulted in handleable white powders.

As $T_g$ can be impacted by technique used to generate dispersions, dispersions were prepared by different methods. For most polymers, little difference in $T_g$ was noted with different methods of preparation. However, for HPMC-P an increase in $T_g$ of ~20° C. was observed for a lyophilized sample compared with a sample prepared by rotary evaporation.

Preparation of solid dispersions involving HPMC was difficult due to the low solubility of HPMC in most solvents. A dispersion was prepared by cryogrinding but it did not exhibit a $T_g$ much higher than that of the rasagiline base.

Solid dispersions of rasagiline citrate prepared were stressed at 75% relative humidity over a period of 24 hours and were compared with rasagiline citrate alone. All solid dispersions except for PVP K-29/32 and PVP-VA showed no moisture accumulation for the first 6 hours by visual inspection. After 6 hours, pooling of moisture was observed in some samples and deliquescence was observed in some samples after 24 hours.

Dispersions containing Eudragit L-100 and HPMC-AS showed no change after 24 hours. All dispersions showed greater stability than rasagiline citrate alone, which was fully deliquesced after 4 hours.

Figure 1:
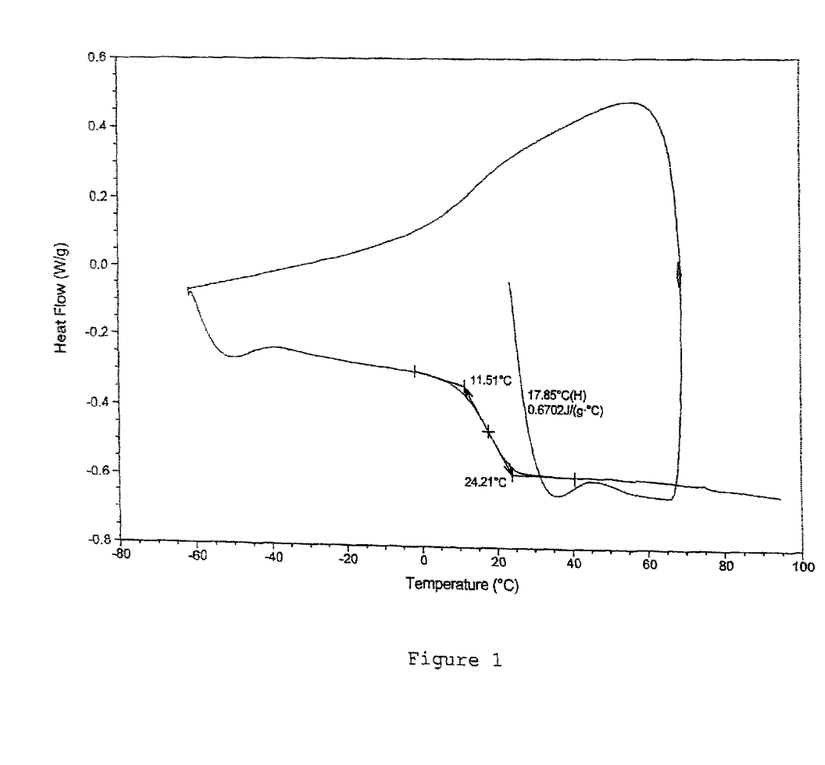
FIG. 1: Cyclic Differential Scanning calorimetry (DSC) thermogram of Rasagiline citrate, sample size 3.43 mg, 20° C./min.
Figure 2:
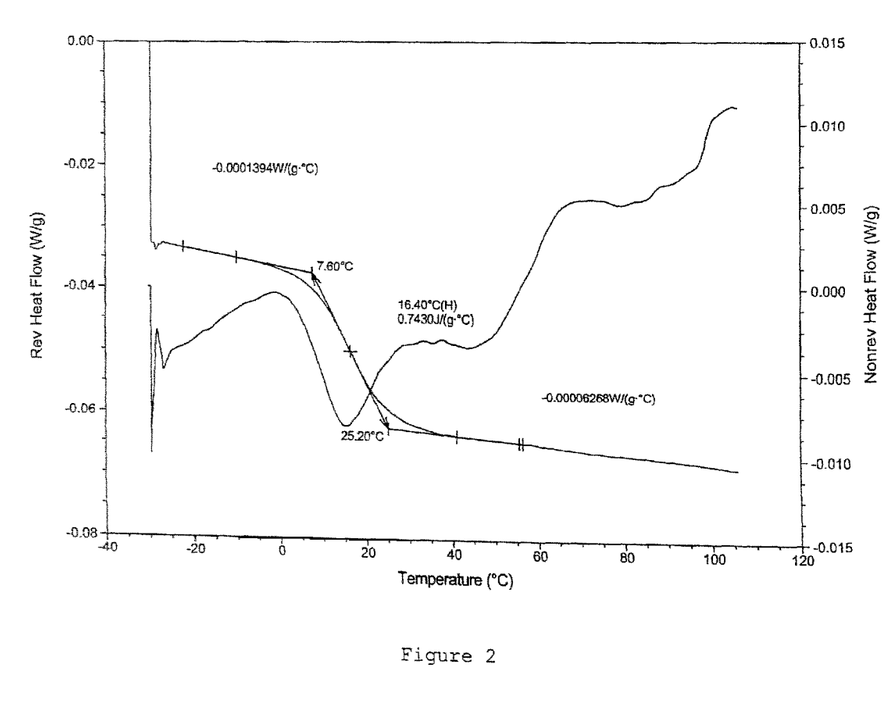
FIG. 2: Modulated Differential Scanning calorimetry (MDSC) thermogram of Rasagiline citrate, sample size 4.00 mg, 2° C./min.
Figure 3:
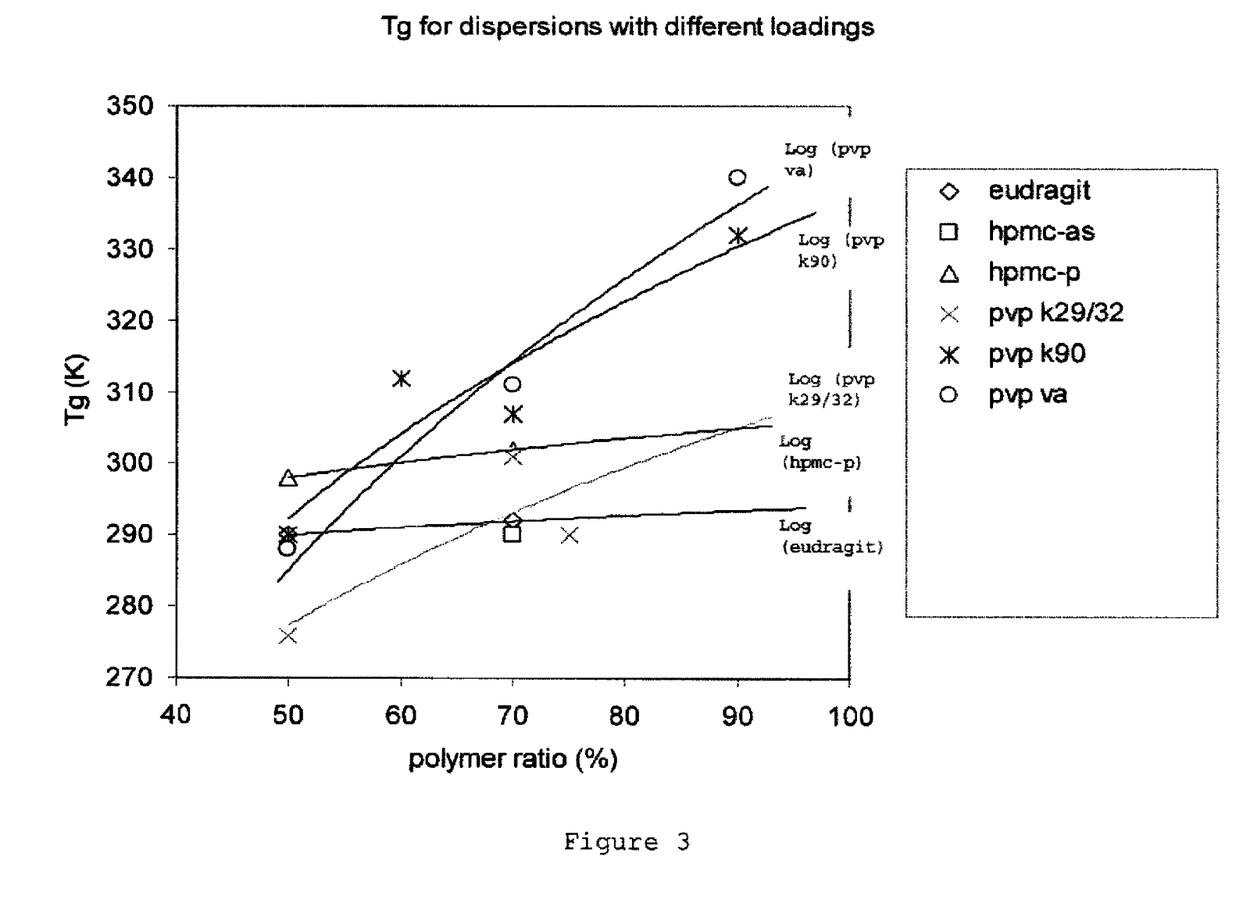
FIG. 3: Trending of glass transition temperature ($T_g$) by varying polymer content

$T_g$ of varying polymer loadings was also studied. As shown in FIG. 3, three dispersions showed a significant increase of $T_g$ with increasing loading of polymers: dispersions containing PVP K-29/32, PVP-VA, and PVP-K90.

Stability of dispersions under high relative humidity was also studied. The results showed that dispersions containing Eudragit L-100 were the most stable and dispersions containing PVP K-29/32 were the least stable. The relative ranking of stability is as follows: Eudragit L-100>HPMC-AS>PVP K-90>HPMCP>PVP-VA>PVP K-29/32.

The invention claimed is:

1. A solid dispersion of at least one polymeric pharmaceutical excipient and rasagiline citrate.

2. The solid dispersion of claim 1, wherein the at least one polymeric pharmaceutical excipient is a water soluble polymeric pharmaceutical excipient.

3. The solid dispersion of claim 1, wherein the rasagiline citrate is mono-rasagiline citrate.

4. The solid dispersion of claim 1, wherein the at least one polymeric pharmaceutical excipient is polyvinylpyrrolidone, hydroxypropyl methylcellulose, hydroxypropyl methylcellulose acetate succinate, or hydroxypropyl methylcellulose phthalate.

5. The solid dispersion of claim 1, wherein the at least one polymeric pharmaceutical excipient is a co-polymer.

6. The solid dispersion of claim 5, wherein the co-polymer is polyvinylpyrrolidone-vinyl acetate or methacrylic acid-ethyl acrylate.

7. The solid dispersion of claim 6, wherein the co-polymer is methacrylic acid-ethyl acrylate.

8. The solid dispersion of claim 1, wherein $T_g$ of the solid dispersion is at least 20° C. higher than that of rasagiline or a pharmaceutically acceptable salt thereof.

9. A pharmaceutical composition comprising the solid dispersion of claim 1.

* * * * *